United States Patent [19]

Bjornson

[11] 4,026,930

[45] May 31, 1977

[54] AZEOTROPIC DISTILLATION OF 1,1,1,3,3,3-HEXAFLUOROISOPROPYL TRIFLUOROACETATE WITH FLUOROTRICHLOROMETHANE

[75] Inventor: Geir Bjornson, Bartlesville, Okla.

[73] Assignee: Phillips Petroleum Company, Bartlesville, Okla.

[22] Filed: May 7, 1976

[21] Appl. No.: 684,349

Related U.S. Application Data

[62] Division of Ser. No. 596,032, July 14, 1975, Pat. No. 3,990,989.

[52] U.S. Cl. .............................. 260/539 A; 203/37; 203/60; 203/67; 260/487; 260/653; 260/633; 204/59 R

[51] Int. Cl.² .......................................... B01D 3/36

[58] Field of Search ................. 203/60, 67, 36, 37; 260/487, 653, 539 A, 633; 204/59 R

[56] References Cited

UNITED STATES PATENTS

| | | | |
|---|---|---|---|
| 3,288,850 | 11/1966 | Nychka et al. | 260/539 A |
| 3,445,507 | 5/1969 | Newallis et al. | 260/487 |
| 3,477,952 | 11/1969 | Bauer et al. | 203/67 |
| 3,894,082 | 7/1975 | Fernschild et al. | 260/539 A |

Primary Examiner—Wilbur L. Bascomb, Jr.

[57] ABSTRACT

1,1,1,3,3,3-Hexafluoroisopropyl trifluoroacetate is separated from a crude reaction mixture by adding fluorotrichloromethane to said mixture and subjecting the resulting composition to fractional distillation to fractionally distill an azeotrope consisting of said 1,1,1,3,3,3-hexafluoroisopropyl trifluoroacetate and said fluorotrichloromethane from the crude mixture.

6 Claims, No Drawings

AZEOTROPIC DISTILLATION OF 1,1,1,3,3,3-HEXAFLUOROISOPROPYL TRIFLUOROACETATE WITH FLUOROTRICHLOROMETHANE

CROSS REFERENCE TO RELATED APPLICATION

This is a division of copending application Ser. No. 596,032 filed July 14, 1975 now U.S. Pat. No. 3,990,989.

BACKGROUND OF THE INVENTION

This invention relates to a novel azeotropic composition containing fluorotrichloromethane and 1,1,1,3,3,3-hexafluoroisopropyl trifluoroacetate.

The 1,1,1,3,3,3-hexafluoroisopropyl trifluoroacetate though a novel compound can be prepared by a number of known processes. For example, U.S. Pat. No. 3,445,507, the disclosure of which is hereby incorporated by reference, teaches the preparation of similar esters by reaction of 1,1,1,3,3,3-hexafluoroisopropanol with appropriate carboxylic acid halides. Electrochemical fluorination to produce similar esters is broadly disclosed in U.S. Pat. Nos. 3,511,716, 3,511,761, and 3,511,762, the disclosures of which are hereby incorporated by reference: 1,1,1,3,3,3-hexafluoroisopropyl trifluroacetate can be produced in the manner broadly described in these patents.

The products formed either by the chemical reaction or by the electrochemical fluorination are generally in admixture with other materials of similar boiling points thus making separation difficult.

SUMMARY OF THE INVENTION

It is the object of this invention to provide a novel azeotropic composition;

it is a further object of this invention to separate 1,1,1,3,3,3-hexafluoroisopropyl trifluoroacetate from crude mixtures containing said acetate;

it is still a further object of this invention to separate fluorotrichloromethane from crude mixtures containing said fluorotrichloromethane; and it is still a further object of this invention to produce 1,1,1,3,3,3-hexafluoroisopropanol.

In accordance with this invention, the constant boiling mixture of fluorotrichloromethane and 1,1,1,3,3,3-hexafluoroisopropyl trifluoroacetate is produced.

DESCRIPTION OF THE PREFERRED EMBODIMENTS

The novel azeotrope of this invention exhibits a boiling point of about 22° C at about 747 torr and contains about 17.5 mol percent 1,1,1,3,3,3-hexafluoroisopropyl trifluoroacetate and 82.5 mol percent fluorotrichloromethane.

This azeotrope can be used to separate 1,1,1,3,3,3-hexafluoroisopropyl trifluoroacetate from crude mixtures containing same by the addition of fluorotrichloromethane or conversely to separate fluorotrichloromethane from crude mixtures containing same by the addition of 1,1,1,3,3,3-hexafluoroisopropyl trifluoroacetate. In either event the resulting mixture is subjected to fractional distillation to recover the constant boiling azeotrope. In the case of crude mixtures which inherently produce a mixture of these two components, the azeotrope can simply be distilled without the addition of any further material or a small amount of the material present in an insufficient amount can be added so as to remove essentially all of both components. Particularly where it is the main object of the operation to recover 1,1,1,3,3,3-hexafluoroisopropyl trifluoroacetate, sufficient fluorotrichloromethane can be added so as to give a total of at least 82.5 mol percent of the trifluorochloromethane based on total mols of this material and the 1,1,1,3,3,3-hexafluoroisopropyl trifluoroacetate.

Fluorotrichloromethane, a component of the novel azeotropic composition of this invention, is a well-known commercially available material.

In the preferred embodiments of the invention, fluorotrichloromethane is added to a crude reaction mixture obtained from the preparation of 1,1,1,3,3,3-hexafluoroisopropyl trifluoroacetate and then the diluted reaction mixture is fractionally distilled to obtain the azeotropic composition of this invention, and thus to separate the ester from by-products, starting materials, etc. In a currently preferred embodiment fluorotrichloromethane can be employed as a diluent or reaction medium for the preparation of 1,1,1,3,3,3-hexafluoroisopropyl trifluoroacetate using any suitable process, such as direct esterification or electrochemical fluorination as described above. Subsequent fractional distillation of the resulting crude reaction mixture, which includes fluorotrichloromethane, then gives the inventive azeotrope in high degrees of purity.

Because of the general characteristic of binary azeotropes which allows the obtaining of the azeotropes from mixtures containing an excess of either of the components, the inventive azeotrope can be obtained from mixtures containing either fluorotrichloromethane or 1,1,1,3,3,3-hexafluoroisopropyl trifluoroacetate in excess of the molar ratio of the components of the azeotrope.

Due to the inert nature of fluorotrichloromethane, the azeotropic composition of this invention can be used without separation of the components for further reactions involving the ester component, such as basic hydrolysis to give 1,1,1,3,3,3-hexafluoroisopropanol and the corresponding salt of trifluoroacetic acid. For instance, the 1,1,1,3,3,3-hexafluoroisopropyl trifluoroacetate can be hydrolyzed using KOH in water to give hexafluoroisopropanol and potassium trifluoroacetate. The 1,1,1,3,3,3-hexafluoroisopropanol is a known solvent for nylon-type polymers and its polymer solutions may be used for coatings, spun fibers, or self-supporting films. Also, it can be converted to hexafluoroacetone which is a known valuable chemical. The potassium trifluoroacetate can be treated with $H_2SO_4$ to recover trifluoroacetic acid.

EXAMPLE

The following run illustrates the preparation of the azeotropic composition of this invention by the reaction of 1,1,1,3,3,3-hexafluoroisopropanol with trifluoroacetyl fluoride in the presence of fluorotrichloromethane as diluent and subsequent distillation of the reaction mixture.

To a stirred 410 cc glass reactor immersed in a cold bath (−6° C to 0° C) were added 44.8 gm pyridine and 70.3 gm fluorotrichloromethane. After the reactor contents cooled to 0° C, 75.5 gm 1,1,1,3,3,3-hexafluoroisopropanol was added. Trifluoroacetyl fluoride (84.3 gm) was added slowly to the vapor phase in the reactor at an overall rate of about 100 gm/hr; however, flow of trifluoroacetyl fluoride into the reactor was intermittent as flow was interrupted periodically in order to maintain the temperature of the reaction mixture between 0° C and 20° C. After completion of trifluoroacetyl fluoride addition (50 min.), the reaction mixture was allowed to warm to 21° C over a five-hour period. Fractional distillation of the resulting reaction mixture gave a fraction (36.4 gm) consisting of an azeotrope boiling at 22° C at 747 torr and containing 17.5 mol percent 1,1,1,3,3,3-hexafluoroisopropyl trifluoroacetate and 82.5 mol percent fluorotrichloromethane, as well as other higher boiling fractions containing predominantly 1,1,1,3,3,3-hexafluoroisopropyl trifluoroacetate.

In order to confirm the existence of the above-described azeotrope which was obtained from an ester-rich mixture, the azeotrope was also obtained by fractional distillation of a fluorotrichloromethane-rich mixture originally containing 69.4 gm fluorotrichloromethane and 14.7 gm of a solution containing about 85 mol percent 1,1,1,3,3,3-hexafluoroisopropyl trifluoroacetate and about 15 mol percent fluorotrichloromethane. The resulting azeotrope (43 gm) possessed the same boiling point and component ratio as described above.

The above-described runs establish the existence, composition and boiling point of the inventive azeotrope.

Chemical shift and multiplicity data of the single proton of 1,1,1,3,3,3-hexafluoroisopropyl trifluoroacetate by proton nmr analysis and fragmentation pattern of the compound by mass spectral analysis were consistent with the assigned structure. The structure was further verified by basic hydrolysis of 1,1,1,3,3,3-hexafluoroisopropyl trifluoroacetate to the known compounds 1,1,1,3,3,3-hexafluoroisopropanol and potassium trifluoroacetate.

While this invention has been described in detail for the purpose of illustration, it is not to be construed as limited thereby but is intended to cover all changes and modifications within the spirit and scope thereof.

I claim:

1. A method of separating 1,1,1,3,3,3-hexafluoroisopropyl trifluoroacetate from a crude reaction mixture obtained from the preparation of 1,1,1,3,3,3-hexafluoroisopropyl trifluoroacetate comprising adding an effective amount of fluorotrichloromethane to said mixture and subjecting the resulting composition to fractional distillation to produce an azeotrope consisting of said 1,1,1,3,3,3-hexafluoroisopropyl trifluoroacetate and said fluorotrichloromethane which is distilled from said mixture.

2. A method according to claim 1 wherein said azeotrope is subjected to basic hydrolysis to convert said 1,1,1,3,3,3-hexafluoroisopropyl trifluoroacetate to 1,1,1,3,3,3-hexafluoroisopropanol and a salt of trifluoroacetic acid.

3. A method according to claim 2 wherein said mixture containing said 1,1,1,3,3,3-hexafluoroisopropyl trifluoroacetate is a product of an electrochemical fluorination process.

4. A method according to claim 3 wherein said basic hydrolysis is carried out utilizing KOH in water to give hexafluoroisopropanol and potassium trifluoroacetate.

5. A method according to claim 1 wherein said mixture containing said 1,1,1,3,3,3-hexafluoroisopropyl trifluoroacetate is a product of an electrochemical fluorination process.

6. A method according to claim 5 wherein the 1,1,1,3,3,3-hexafluoroisopropyl trifluoroacetate from said azeotropic composition is hydrolyzed utilizing KOH in water to give hexafluoroisopropanol and potassium trifluoroacetate.

* * * * *